US00PP14411P39

(12) United States Plant Patent
Furukawa

(10) Patent No.: US PP14,411 P3
(45) Date of Patent: Dec. 23, 2003

(54) BRACTEANTHA PLANT NAMED 'SUN YELLOW BON BON'

(50) Latin Name: *Bracteantha bracteata*
Varietal Denomination: Sun Yellow Bon Bon

(75) Inventor: Hiroaki Furukawa, Yamanshi (JP)

(73) Assignee: Miyoshi & Company Ltd. (JP)

( * ) Notice: Subject to any disclaimer, the term of this patent is extended or adjusted under 35 U.S.C. 154(b) by 0 days.

(21) Appl. No.: 10/286,703

(22) Filed: Nov. 1, 2002

(65) Prior Publication Data

US 2003/0188367 P1 Oct. 2, 2003

Related U.S. Application Data

(63) Continuation of application No. 10/113,592, filed on Apr. 1, 2002.

(51) Int. Cl.[7] ..... A01H 5/00

(52) U.S. Cl. ..... Plt./359

(58) Field of Search ..... Plt./359

*Primary Examiner*—Bruce R. Campell
*Assistant Examiner*—Annette H. Para
(74) *Attorney, Agent, or Firm*—Wood, Phillips, Katz, Clark & Mortimer

(57) ABSTRACT

A new and distinct Bracteantha plant named 'Sun Yellow Bon Bon', characterized by its yellow colored involucral bracts and yellow disc florets, dark green leaves, good basal branching character and upright mounded growth habit.

1 Drawing Sheet

Latin name of the genus and species of plant claimed: *Bracteantha bracteata.*
Variety denomiantion: 'Sun Yellow Bon Bon'.

BACKGROUND OF THE INVENTION

The present invention comprises a new and distinct Bracteantha plant, botanically known as *Bracteantha bracteata* and hereinafter referred to by the cultivar name 'Sun Yellow Bon Bon'.

The new cultivar was developed by the inventor through a controlled breeding program at Kitakoma-gun, Yamanashi, Japan in February 1995.

The female (seed) parent of 'Sun Yellow Bon Bon' was the an unnamed wild creeping type with yellow flowers, dark green leaves and compact, creeping habit (not patented in the United States). The male (pollen) parent of 'Sun Yellow Bon Bon' was the seedling selection No. 1109 (not patented in the United States) which exhibits pink flowers, light green foliage, compact and upright habit. 'Sun Yellow Bon Bon' was selected as one of the flowering progeny of the above cross.

Asexual reproduction of the new cultivar by terminal cuttings, at West Chicago, Ill., has demonstrated that the characteristics of the new cultivar as herein described are firmly fixed and retained through successive generations of such asexual propagation.

SUMMARY OF THE INVENTION

It was found that the cultivar of the present invention:

(a) exhibits yellow involcural bracts and yellow disc florets;

(b) forms dark green foliage;

(c) exhibits a good basal branching character; and (d) exhibits an upright mounded growth habit.

When the new cultivar of the present invention is compared to Dreamtime 'Cream' (disclosed in U.S. Plant patent application Ser. No. 09/819,340) it is found that the new cultivar is more vigorous and has smaller flowers of a darker yellow color.

BRIEF DESCRIPTION OF PHOTOGRAPH

The accompanying photograph show as nearly true as it is reasonably possible to make the same in color illustrations of this type, typical flower and foliage characteristics of the new cultivar. The plants were grown for 14 weeks in a greenhouse at West Chicago, Ill.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Feb. 15, 2002. The readings were taken between 10:00 and 11:00 a.m. under natural daylight conditions. The plants were produced from cuttings taken from stock plants and grown for 14 weeks in a double polycarbonate covered greenhouse under conditions comparable to those used in commercial practice while utilizing a soilless growth medium. Temperatures of approximately 65° to 75° (18° to 24° C.) during the day and approximately 55° to 60° F. (13° to 16° C.) during the night and light levels of between 5,000 and 8,000 foot candles were maintained.

Classification:
*Botanical.*—*Bracteantha bracteata* cultivar 'Sun Yellow Bon Bon'.
*Commercial.*—Helichrysum.

Parentage:
*Female parent.*—Unnamed, wild creeping type.
*Male parent.*—Proprietary seedling selection No. 1109.

Propagation:

*Type cutting.*—Terminal tip.

*Time to initiate roots.*—Approximately 21 to 30 days with the shorter times generally being experienced in the summer and the longer times in the winter.

Plant description:

*Habit of growth.*—Moderate. A mature plant, 14 weeks after the planting of a rooted cutting, commonly measures approximately 21 cm in height and approximately 47 cm in diameter.

*Branching habit.*—Freely basal branching although pinching improves basal branching. Commonly develops approximately 4 lateral branches.

*Form.*—Upright, mounded.

*Lateral branch.*—Length: Approximately 23.5 cm. Diameter: Approximately 5 mm. Texture: Hirsute. Color: 145A. Internode length: Approximately 9 mm.

*Foliage.*—Arrangement: Alternate. Shape: Lanceolate with entire margin, acute apex and clasping base. Size: Approximately 4.3 cm in length and approximately 6 mm at widest point. Upper surface is rough and 137A. Lower surface is smooth and 137C. Midvein on lower surface is moderately pubescent. Venation of both surfaces: Closest to 145A.

*Flowering description:*

*Flowering habit.*—Freely flowering.

*Natural flowering season.*—Spring through fall.

*Inflorescence type.*—Single, composite, persistent.

*Flowers arrangement.*—Acropetally on a capitulum.

*Bud.*—Size: 1.6 cm in length and 1.4 cm in diameter. Color: 12A at base; 22A at tip.

*Inflorescence diameter.*—Approximately 3 cm.

*Inflorescence depth.*—1.5 cm.

*Involcural bracts.*—Quantity: Approximately 8 whorls. Aspect: Flat . Appearance: Smooth, papery. Shape: Linear. Size: Length — 1.5 cm, width varies from 1 to 4 mm. Color — Upper and lower surface, fully opened: 12A. Outer 2 whorls have tips of 165A.

*Disc diameter.*—1.2 cm.

*Disc florets.*—Shape: Tubular. Length: Approximately 5 mm.

*Peduncle.*—Length: Approximately 5 cm. Diameter: Approximately 2 mm. Strength: Good. Aspect: Erect. Color: 145A. Texture: Puberulent.

*Fragrance.*—None.

*Reproductive organs.*—Stigma color 25A. Pollen color: 21A.

Seed production: Seed production has not been observed.

Disease resistance: Resistance to diseases common to Bracteantha has not been observed.

I claim:

1. A new and distinct cultivar of Bractheantha named 'Sun Yellow Bon Bon' substantially as herein shown and described, which:

(a) exhibits yellow involcural bracts and yellow disc florets;

(b) forms dark green foliage;

(c) exhibits an upright mounded growth habit; and (d) exhibits a good basal branching character.

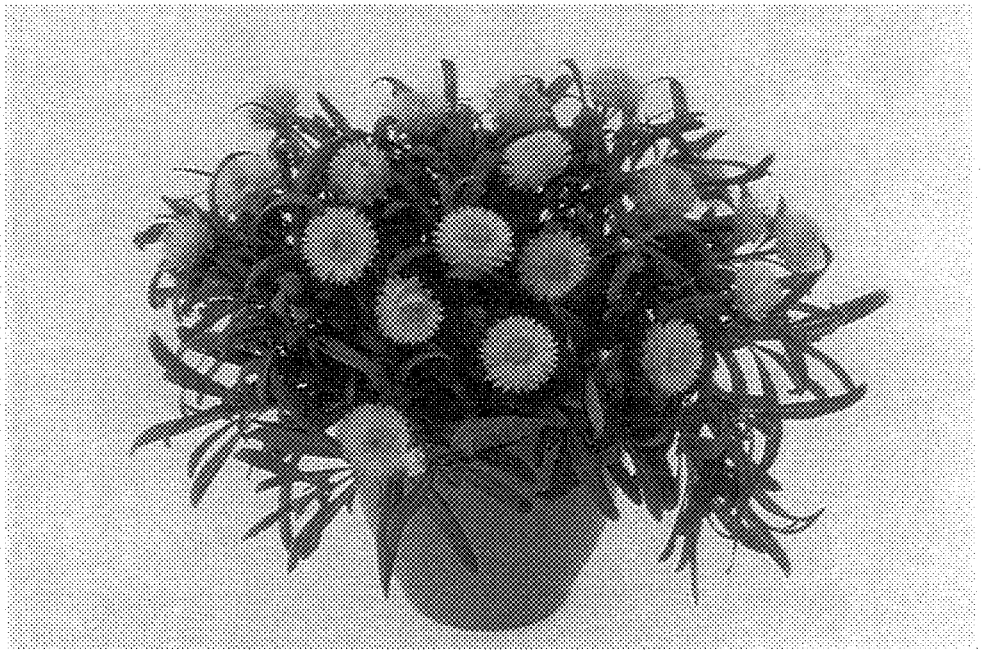

* * * * *